United States Patent [19]
Johnsen et al.

[11] Patent Number: 5,167,650
[45] Date of Patent: Dec. 1, 1992

[54] POUCH WITH MOUNTING MEMBER FOR REMOVABLE ADHESIVE FILTER

[75] Inventors: Kenneth A. Johnsen, Piscataway; Frank Freeman, Lawrenceville, both of N.J.

[73] Assignee: E. R. Squibb, Princeton, N.J.

[21] Appl. No.: 775,807

[22] Filed: Oct. 11, 1991

Related U.S. Application Data

[63] Continuation of Ser. No. 367,237, Jun. 16, 1989, Pat. No. 5,085,652.

[51] Int. Cl.⁵ ............................................. A61F 5/44
[52] U.S. Cl. .................................. 604/332; 604/333; 604/905
[58] Field of Search .................... 604/86, 87, 88, 905, 604/405, 406, 415, 411, 414, 337–344

[56] References Cited

U.S. PATENT DOCUMENTS 4,268,286  5/1981  Steer et al. ..................... 604/333
4,567,999  2/1986  Hjertman et al. ................ 604/411

FOREIGN PATENT DOCUMENTS 2202746  10/1988  United Kingdom ............... 604/333

Primary Examiner—Randall L. Green
Assistant Examiner—K. Reichle
Attorney, Agent, or Firm—James & Franklin

[57] ABSTRACT

An annular mounting member is bonded to the pouch wall to define a vent opening. The mounting member is made of material which is compatible with the pouch film and has a smooth exterior surface adapted to facilitate removable mounting of an adhesive coated element in alignment with the opening. The element may be a deodorizing filter assembly including a filter disk surrounded by an annular border member coated with pressure sensitive adhesive or a gas impermeable cover member designed to close the vent.

9 Claims, 7 Drawing Sheets

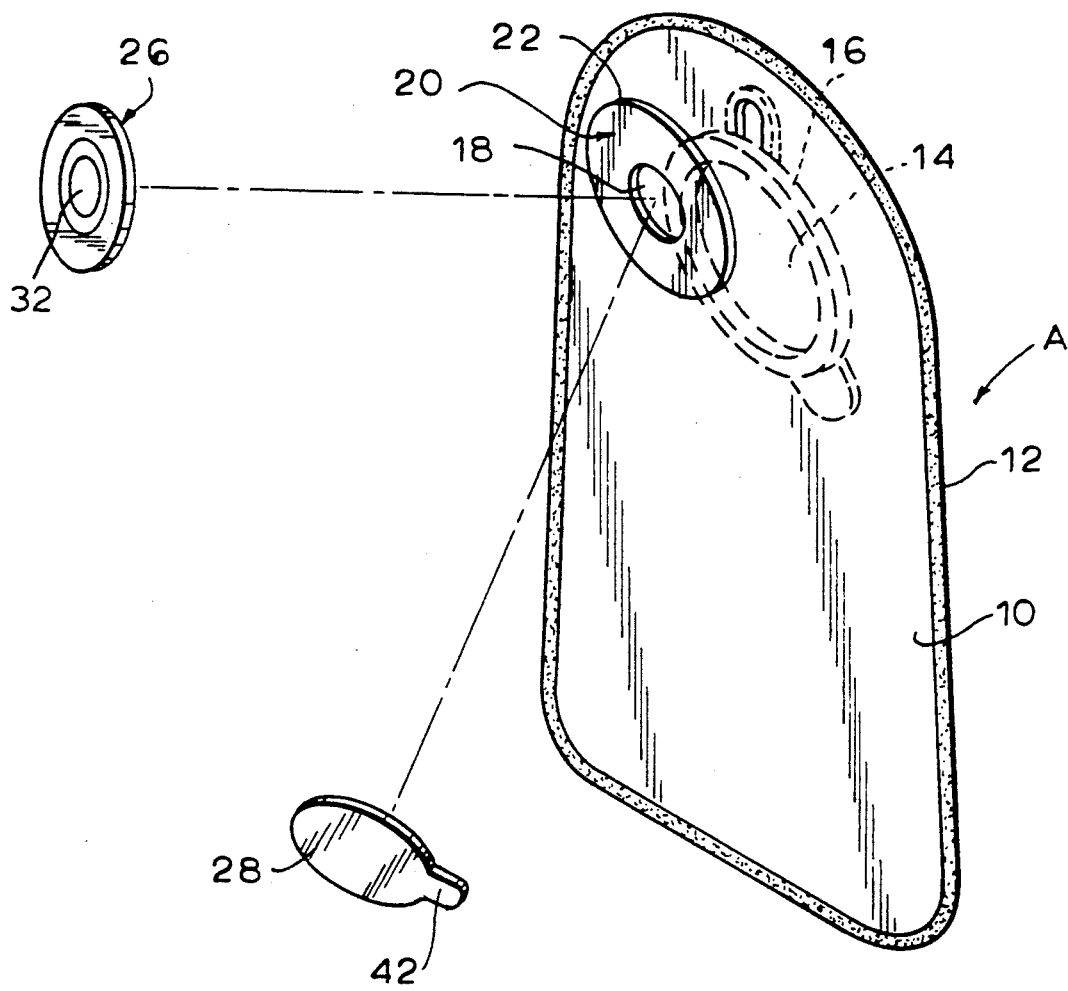
F I G. 1

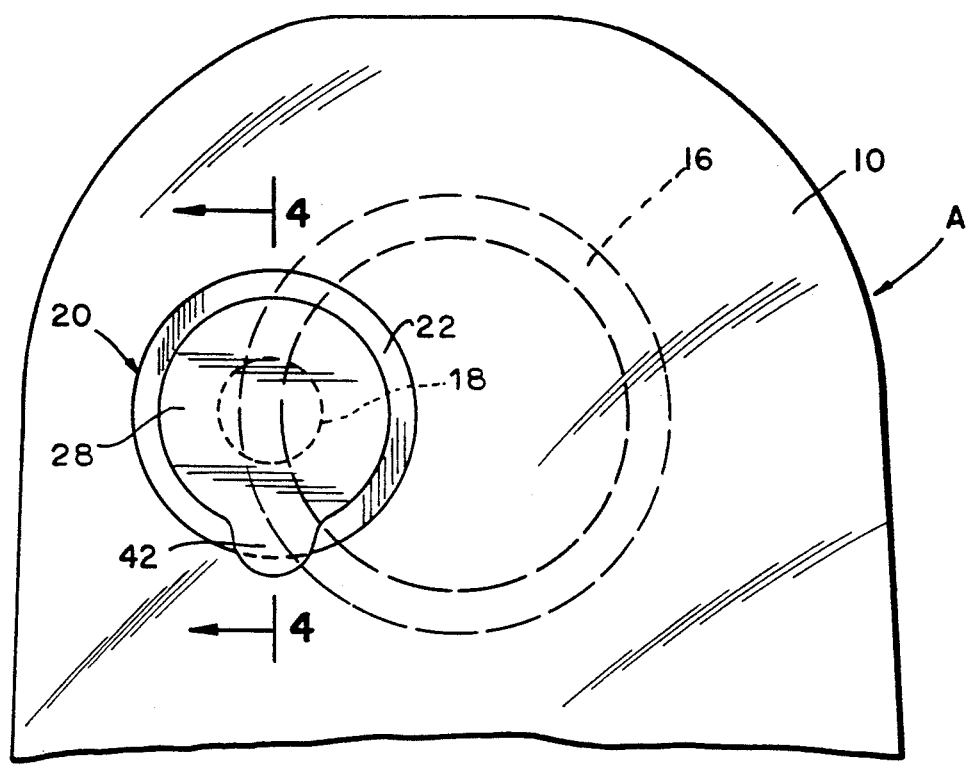
FIG. 2
FIG. 3
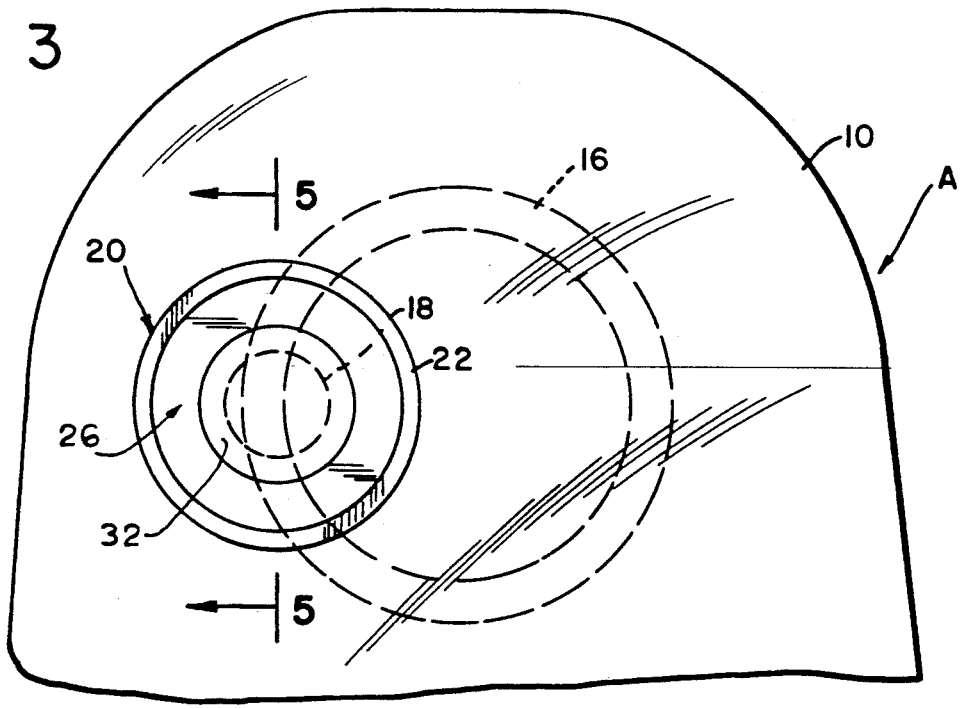

POUCH WITH MOUNTING MEMBER FOR REMOVABLE ADHESIVE FILTER

This is a divisional of co-pending application Ser. No. 367,237, filed on Jun. 16, 1989, now U.S. Pat. No. 5,085,652.

The present invention relates to medical devices of the type including collection receptacles with deodorizing filters and more particularly with a medical device which includes a collection receptacle or pouch having a mounting member bonded thereto and adapted to facilitate removable mounting of a deodorizing filter assembly or cover element.

BACKGROUND OF THE INVENTION

Certain surgical procedures, such as colostomies, ileostomies or urostomies result in a surgically created opening or stoma in the abdominal wall through which bodily wastes are discharged. Because the patient has no control over the discharge, an appliance is utilized which includes a collection receptacle in the form of a pouch or bag which is affixed to the patient in alignment with the stoma. The appliance collects waste as it is discharged and also protects the stoma.

Other medical procedures, such as wound care or irrigation, also utilize devices which include a collection receptacle. Such receptacles may be in the form of a pouch or bag as well.

Such collection pouches or bags are often formed of thin sheets of material welded along the periphery. The materials are generally composed of light weight, odor proof, flexible polymeric plastic.

Because a portion of the material to be collected is often gaseous, a problem arises with respect to the distention of the pouch due to the accumulation of gas, a great disadvantage in an ostomy system, for example, which is designed to be inconspicuous and permit the ostomate to engage in normal physical activity without embarrassment. To overcome the problem of accumulated gases, many devices utilize a configuration which permits venting of the gas. However, the venting of gases often presents a problem with respect to odor. In order to eliminate odor as the gas is vented, deodorizing filters have been employed.

The gas venting problem has been subjected to a variety of different solutions. Some pouches have been provided with a tortuous path vent opening, with or without a deodorizing filter. Others have been provided with openings in the pouch wall, covered with deodorizing filters. Another approach has been to provide replaceable filters attached to the bag by a series of plural sequentially peelable adhesive members.

Certain ostomy systems, such as that disclosed in U.S. Pat. No. 4,460,363 to Steer et al., permit pouches to be removed and reused, hence prolonging the useful life of the pouch beyond the useful life of a single filter. It is therefore often necessary that the deodorizing filter itself be replaced periodically in order to insure that complete deodorization is taking place. On the other hand, it may be desirable, in certain instances, to eliminate the deodorizing filter completely, and simply seal the vent. Accordingly, it is most desirable to have a structure where the filter can be removed as necessary so that it can be replaced or the vent can be obstructed. The use of adhesive coated elements is particularly well adopted for this purpose.

Prior art pouches adapted for use with filters either have had the filters permanently bonded to the pouch wall, such as by heat or impulse welding or, if removable filter mounting is employed, the filter is adhesively mounted directly to the pouch wall surrounding the vent opening. However, the pouch wall is made of a material which, in the latter case, does not permit an adhesive element to be easily removed and replaced. Because the pouch wall is so thin, an adhesive strong enough to make the required seal will often cause the wall to tear around the vent opening as the filter is removed, clearly a severe disadvantage. In addition, the pouch wall is so thin surrounding the vent opening that it tends to wrinkle, preventing a good seal with adhesive coated filter.

OBJECTS OF THE INVENTION

To overcome the above difficulties, a pouch has been designed with a mounting member permanently affixed to the pouch wall surrounding the vent opening. The mounting member is made of a material which is compatible with the pouch film such that it can be permanently bonded thereto. It has an exterior surface which is adapted to facilitate sealing engagement with an adhesive coated element, which may be a filter assembly or a cover element. The mounting member serves to increase the effectiveness of the adhesive seal by providing a wrinkle-free mounting surface compatible with the adhesive and at the same time prevent the pouch wall from being torn along the vent opening as the adhesive element is removed therefrom.

It is, therefore, a prime object of the present invention to provide a pouch with a mounting surface for a removable adhesive filter assembly.

It is another object of the present invention to provide a pouch with a mounting member which is made of material which is compatible with the material of the pouch wall.

It is another object of the present invention to provide a pouch with a mounting member which has an annular configuration and is affixed to the pouch wall surrounding the vent opening.

It is another object of the present invention to provide a pouch with a mounting member for an adhesive filter of the type which permits gaseous flow in a direction perpendicular to its surface.

It is another object of the present invention to provide a pouch with a mounting member for an adhesive filter assembly of the type which includes a filter disk surrounded by a border member coated with adhesive.

It is another object of the present invention to provide a pouch with a mounting member which permits a cover member to be affixed thereto when the filter is absent.

In accordance with one aspect of the present invention, a device is provided comprising a collection receptacle in the form of a thin walled pouch. The pouch comprises a vent through which gaseous matter may escape. A mounting member is affixed to the pouch wall, surrounding the vent. The member has an opening aligned with the vent such that the passage of gases through the vent is substantially unobstructed. The member has an exterior surface adapted to facilitate removable mounting of an adhesive element in alignment with the vent.

The mounting member is composed of a material which is compatible with the material of the pouch wall. Preferably the mounting member is composed of a mixture of polyethylene and ethylene vinyl acetate. Preferably, it is annular in configuration.

The removable element may be in the form of gas impermeable cover element coated with a pressure sensitive adhesive. Preferably, the cover element has a substantially circular configuration with a radially extending tab.

Alternatively, the removable element may comprise a filter assembly including a filter disk and a means for encapsuling the filter disk. The filter disk may comprise an open cell foam treated with activated carbon. The encapsulating means may comprise thin sheets of microporous film between which the filter disk is sandwiched. The films preferably have a bonded edge and are preferably treated to be liquid impervious.

A substantially annular border member is provided as part of the assembly. The border member is composed of a closed cell foam. It is preferably coplanar with and surrounds the filter disk. Preferably, the border member is coated with a pressure sensitive adhesive layer. An exterior film layer may be provided with an opening. The exterior layer is bonded to the filter disk and the border member.

In accordance with another aspect of the present invention, a device is provided including a collection receptacle in the form a thin walled pouch. The pouch has a vent through which gaseous matter may escape. A mounting member is affixed to the pouch wall surrounding the vent. The member has an opening aligned with the vent such that passage of gases through the vent is substantially unobstructed. The member is adapted to permit removable mounting of an adhesive coated filter element in alignment with the opening such that gases are filtered through the element as they pass from the pouch.

In accordance with another aspect of the present invention, a device is provided comprising a collection receptacle in the form of a thin walled pouch. The pouch includes a vent through which gaseous matter may escape. A mounting member is affixed to the pouch wall surrounding the vent. The member has an opening aligned with the vent such that the passage of gases through the vent is substantially unobstructed. The mounting member is adapted to permit removable mounting of a cover element over the opening such that gases are prevented from escaping through the vent.

In accordance with another aspect of the present invention, a device comprising a collection receptacle in the form of a thin walled pouch is provided in combination with a member affixed to the wall of the pouch and punch means for creating a vent through the member and wall. The member, once punched, defines a boarder surrounding the vent adapted to facilitate removable mounting of a filter assembly in alignment with the vent.

The punch means preferably comprises first and second hingeably connected parts. A protrusion extends from one of the parts. A recess is formed in the other of the parts. The protrusion and the recess are adapted to align with the member therebetween.

Means are provided for adhesively mounting the filter assembly to the member. The filter assembly preferably comprises a filter disk, microporous film for encapsulating the disk and an annular border member. Preferably the border member is coated with an adhesive.

BRIEF DESCRIPTION OF THE DRAWINGS

To these and such other objects which may hereinafter appear, the present invention relates to an ostomy pouch with a mounting member for an adhesive filter, as set forth in detail in the following specification and recited in the annexed claims, taken together with the accompanying drawings, wherein like numerals refer to like parts, and in which:

FIG. 1 is an exploded isometric view of an ostomy pouch including the mounting members of the present invention, showing a cover member and a filter element alternately mountable thereon.

FIG. 2 is a plan view of the top portion of the rear of the pouch wall showing a cover element mounted thereon;

FIG. 3 is a view similar to FIG. 2 but showing the pouch with a filter element mounted thereon;

DESCRIPTION OF THE INVENTION

Figure 4:
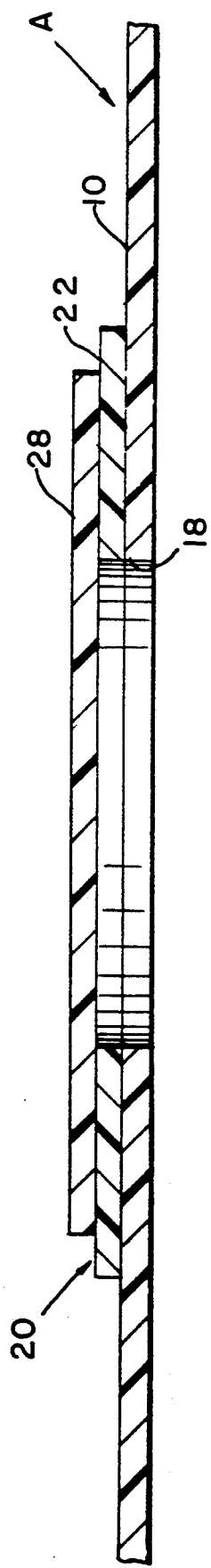
FIG. 4 is a cross-sectional view taken along line 4—4 of FIG. 2.

As seen in FIGS. 1 through 5, the first preferred embodiment of the present invention includes a collection receptacle in the form of a pouch, generally designated A. Pouch A includes a rear wall 10 and a front wall 12 made of thin, flexible, preferably transparent, film which is heat welded around the periphery to form an enclosed receptacle.

Although the pouch A which is illustrated has no outlet, an outlet may be provided as is conventional. The pouch illustrated in the drawings is of the type utilized in a so-called "two-piece" ostomy appliance; that is, an appliance in which the pouch is detachably mounted to an adhesive coated dressing designed to be affixed to the body surrounding the stoma. It should be appreciated that while the present invention is illustrated in conjunction with a detachable pouch of the closed variety, it is equally applicable to one-piece type appliances wherein the pouch is permanently affixed to the dressing. The particular configuration of the pouch plays no portion in the present invention which is equally applicable to all pouch styles.

The films from which the pouch may be made are selected from materials which possess the properties of being moisture impermeable, odor impermeable and capable of being heat sealed or impulse welded. Suitable materials include polyethylene, copolymers of polyethylene and ethylene vinyl acetate, copolymers of vinyl chloride and polyvinylidene chloride and lamanents thereof. The pouch walls are preferably from about 2-4 mils thick.

Wall 12 is provided with a stoma receiving opening 14 which is defined by a coupling ring 16 of the type which is conventional in two-piece ostomy devices such as those disclosed in Steer U.S. Pat. No. 4,460,363.

Rear wall 10 is provided with a circular vent 18 which is preferably centered approximately in alignment with a portion of the coupling ring 16. Surrounding vent 18 is a mounting member 20 which is permanently affixed or laminated to the pouch wall surrounding the vent. Member 20 preferably has an annular configuration.

Mounting member 20 is made of a material which exhibits superior characteristics when a pressure-sensitive adhesive is applied to it and peeled from it. The thickness of the mounting member eliminates folds and wrinkles in the pouch film which prevent a fluid tight seal between the wall and the filter assembly. Stress exerted on the pouch film as a filter is removed is more evenly distributed by the mounting member, preventing tears in the film which otherwise would start adjacent at the vent.

Figure 5:
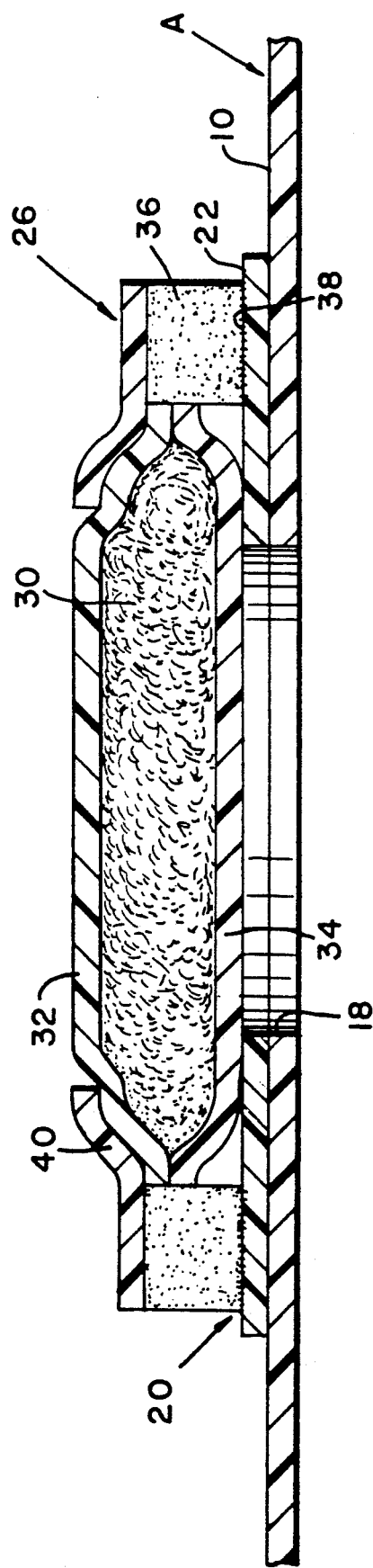
FIG. 5 is a cross-sectional view taken along line 5—5 of FIG. 3.
Figure 6:
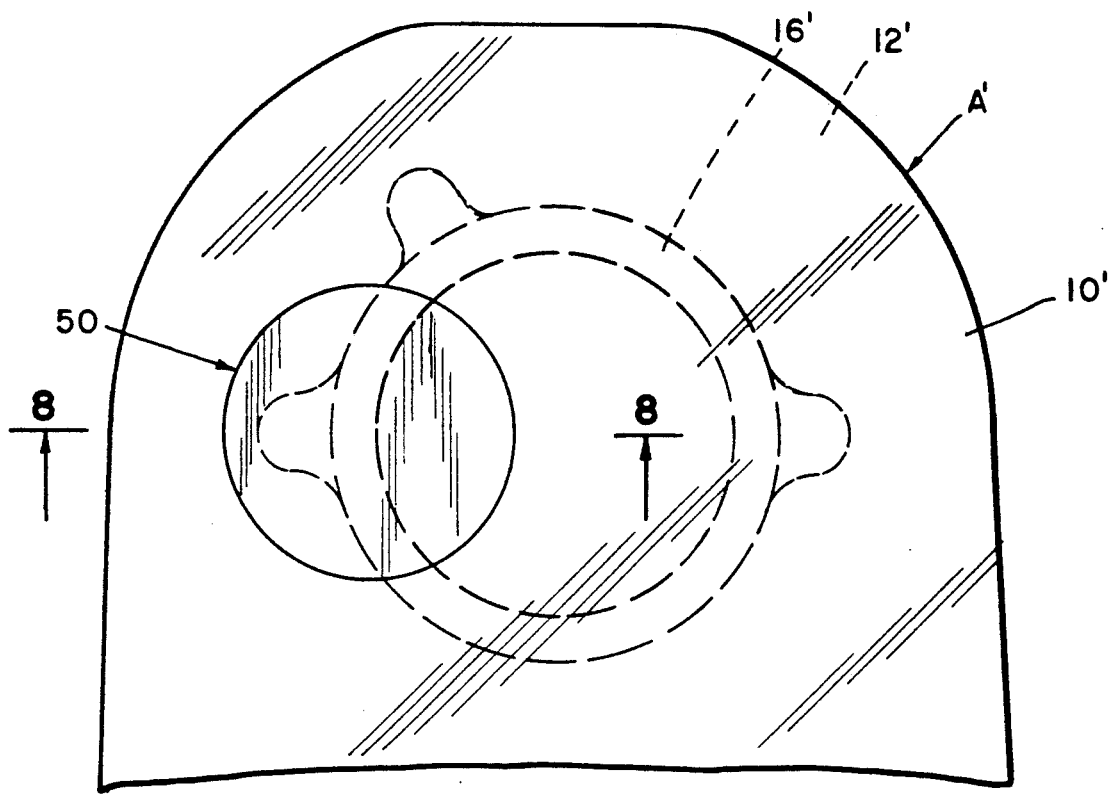
FIG. 6 is a plan view of the top portion of the rear of a pouch wall illustrating a second preferred embodiment of the present invention.

The mounting member preferably comprises a blend of polyethylene and ethylene vinyl acetate which is compatible with the pouch film. As best seen in FIGS. 4 and 5, mounting member 20 comprises a disk 22 affixed to the outer surface of wall 10 surrounding opening 18.

As illustrated in the drawings, mounting member 20 is adapted to affix either a filter assembly, generally designated 26 or cover member 28 over the vent. It should be appreciated that the vent in member 20 is preferably relatively large so as not to become obscured by solid or semi-solid waste.

While a variety of different filter assemblies may be utilized, it is preferable to use an assembly which permits movement of gas therethrough in a direction substantially perpendicular to its surface. The filter assembly illustrated in the drawings is of the type described in Steer U.S. Pat. No. 4,668,258 and is believed to be preferable for this purpose. However, the precise structure of the filter assembly plays no part in the structure of the filter assembly plays no part in the present invention and should not be considered a limitation thereto.

As best seen in FIG. 5, the filter assembly preferably comprises a disk of foamed, open cell non-woven synthetic polymeric material, for example, polyurethane having a large number of activated carbon particles distributed over its major surface. This foam disk 30 is then laminated between two thin sheets of a heat sealable microporous film 32, 34, such as polyurethane which is preferred, polyethylene, polyvinylchloride, etc. The surface of sheet 34 which will face the pouch is preferably treated with a water repellant such as polytetrafluorethylene (PTFE), fluorinated ethylenepropalene (FEP), silicone or wax.

One material which is suitable for use as disk 30 is commercially available under the trade name BONDINA. Another type of suitable deodorizing material is a felt pad impregnated with activated charcoal in fine particulate form. Various types of such carbon cloth are commercially available.

Filter disk 30 is surrounded by an annular border member 36, preferably fabricated of a closed cell foam with a pressure sensitive adhesive layer 38. A top film layer 40 with a center hole for gas flow is bonded to the exterior surface of border member 36 and the filter disk.

This construction, including the foam border member 36, makes the filter easier to handle, apply and remove, particularly for patients with poor dexterity. The mass of the foam also keeps the filter assembly flat for wrinkle-free applications.

Accordingly, filter assembly 26 forms a stick-on deodorizing filter particularly well suited for removing odors from ostomy and wound care pouches. The odors are absorbed as they pass through the open cell foam treated with activated carbon. The backing of the filter assembly is coated with a pressure-sensitive adhesive which allows placement over the vent in the pouch.

When the filter loses its deodorizing abilities, it is simply peeled off and replaced with a new filter assembly. The soft, flexible construction of the filter conforms to bends in the pouch and the wearer's body, making this device comfortable and inconspicuous under clothing. The filter is water-repellent and may be worn while showering or bathing.

In the event that the user does not wish to use a filter, vent 18 can be sealed through the use of a simple cover element 28. Cover element 28 is preferably a thin, gas and liquid impervious plastic disk, coated with an adhesive layer which affixes to disk 22 of the mounting member 20, as illustrated in FIGS. 2 and 4. For convenience, cover element 28 is provided with an outwardly extending gripping tab 42 which is preferably not coated with adhesive such that the cover member can be more easily gripped and removed.

The second preferred embodiment of the present invention, as illustrated in FIGS. 6 through 11, includes a pouch A' with a rear wall 10' and a front wall 12' with a coupling ring 16', all of which are virtually identical to that illustrated in FIGS. 1 through 5. In the second preferred embodiment, mounting member 20 has been replaced by a circular mounting member 50 which, unlike mounting member 20, has no central opening. Mounting member 50 is, however, made of the same material as mounting member 20 and is preferably situated at the same location on the pouch.

Figure 8:
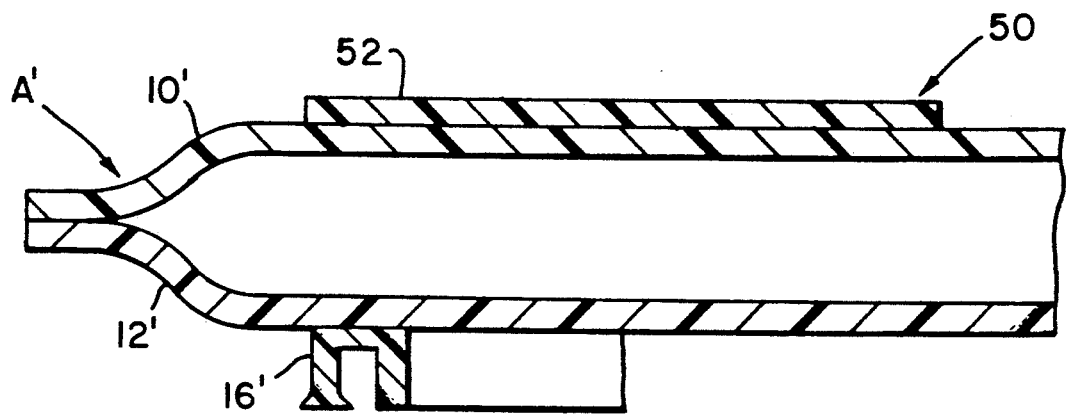
FIG. 8 is a cross-sectional view of the pouch wall illustrated in FIG. 6 taken along line 8—8.

As shown in FIG. 8, mounting member 50 comprises a circular disk 52 situated on outer surface of pouch wall 10'. As will be appreciated from FIG. 8, pouch wall 10' has no vent therein when supplied to the patient.

Figure 7:
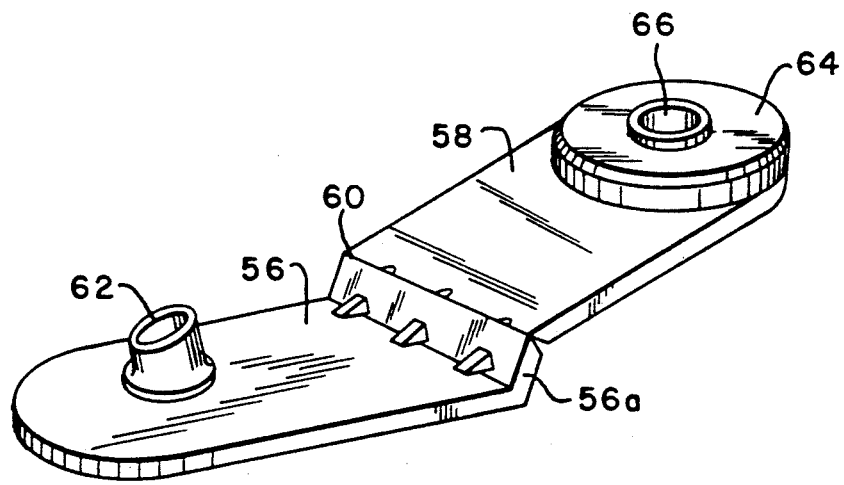
FIG. 7 is an isometric view of a punch used in conjunction with the pouch illustrated in FIG. 6.
Figure 9:
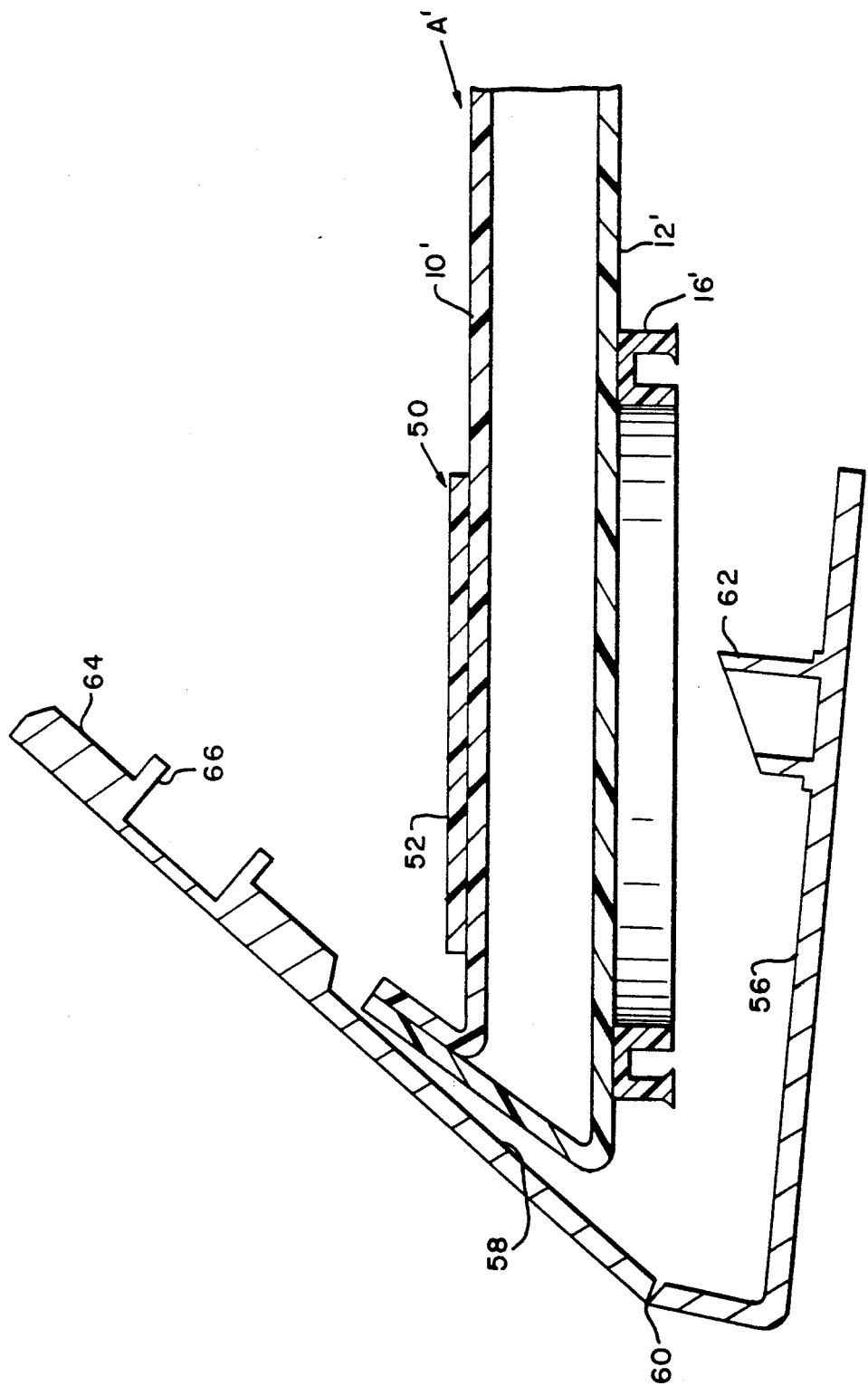
FIG. 9 is a cross-sectional view showing the punch of FIG. 7 in the open position, with a portion of the pouch therein.
Figure 10:
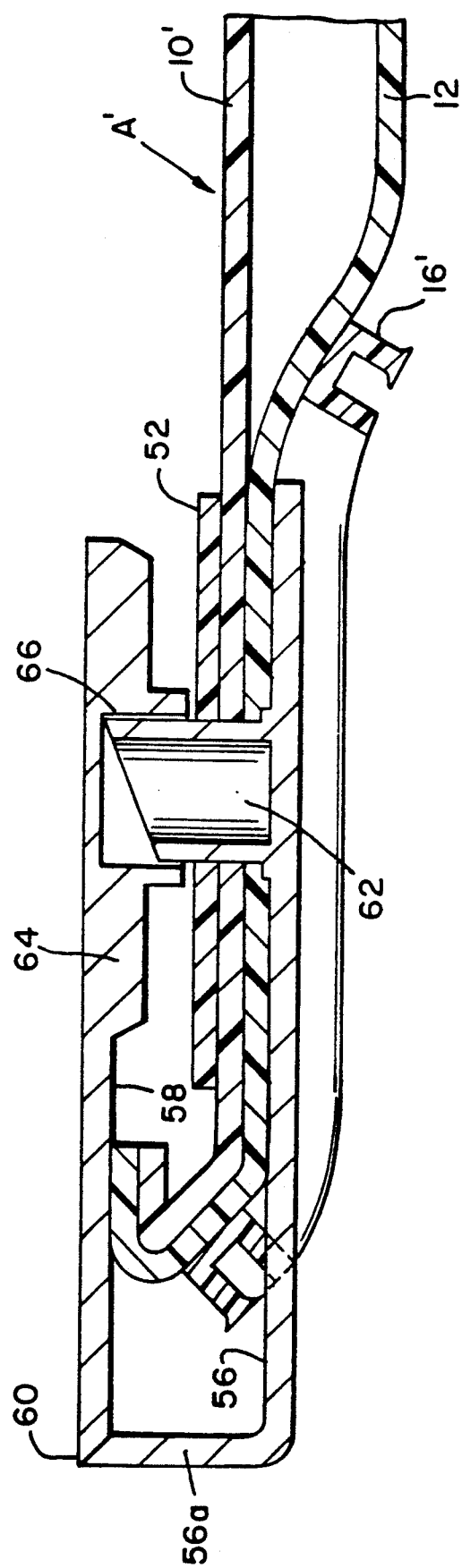
FIG. 10 is a view similar to FIG. 9 but showing the punch in the closed position.

In order to create a vent through mounting member 50 and wall 10' of the pouch, a punch of the type illustrated in FIGS. 7, 9 and 10 is provided. As best seen in FIG. 7, the punch includes first and second substantially planar elements 56, 58 which are hingeably connected by means of a living hinge 60. The interior surface of element 56 is provided with an outwardly extending protrusion 62 preferably having a substantially tubular configuration with an inclined rim.

Situated on the interior surface of element 58 is an annular member 64 defining a recess 66 which, when elements 56 and 58 are situated in substantially parallel planes, will align with protrusion 62.

Figure 11:
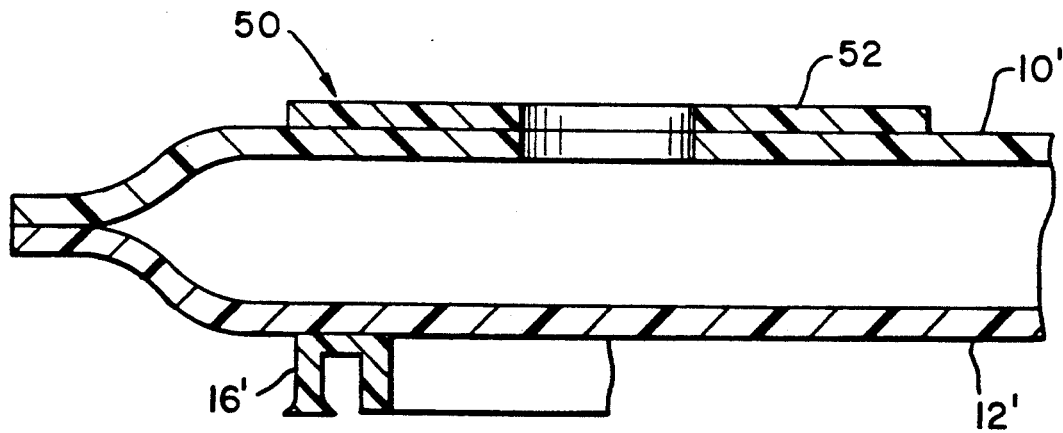
FIG. 11 is a cross-sectional view similar to that shown in FIG. 8 but illustrating the pouch after the vent has been punched.

As best seen in FIG. 9, in order to punch a vent through wall 10' and mounting member 50, pouch A' is situated between elements 56 and 58 with protrusion 62 aligned with the inlet opening defined by coupling ring 16' on wall 12' and further aligned with mounting member 50. The punch is then closed, as illustrated in FIG. 10, such that protrusion 62 is received within opening 66 and a vent 70 is punched in the pouch wall and through the mounting member, as illustrated in FIG. 11. It will be noted that when the punch is closed, elements 56 and 58 assume a substantially parallel position because element 56 has a portion 56a which is substantially perpendicular to the remainder of element 56 and which is connected to portion 58 by means of hinge 60. The length of section 56a is approximately equal to the length of protrusion 62 such that when the punch is closed the elements are substantially parallel.

After the punch has formed the vent in the pouch wall and the circular mounting member, the pouch will appear substantially as shown in FIGS. 1 through 5. It may then be utilized with a filter assembly 26 or cover member 28 precisely as described above.

It will now be appreciated that the present invention relates to a pouch or the like which has a mounting member affixed to its wall which is formed of material which will protect the pouch wall from tearing or wrinkling and at the same time be more compatible with an adhesive to facilitate use of a removable filter assembly. In a first embodiment, the mounting member is annular, having a vent formed when the pouch is fabricated. In a second preferred embodiment, the pouch is provided with a circular mounting member with no vent therein and a punch which is adapted to be utilized to provide a vent through the mounting member and pouch wall. The pouch of the present invention may be utilized with a filter assembly of conventional structure coated with known adhesives.

While only a limited number of preferred embodiments have been disclosed for purposes of illustration, it is obvious that many variations and modifications could be made thereto. It is intended to cover all of these variations and modifications which fall within the scope of the present invention as defined by the following claims:

We claim:

1. In combination, an ostomy device comprising a collection receptacle in the form of a pouch having first and second walls, one of said walls having a waste receiving opening therethrough, means for fluidically coupling said waste receiving opening to a stoma of a patient, a filter mounting means permanently affixed to the exterior surface of the other of said walls in alignment with the waste receiving opening and separate punch means comprising first and second hingeably connected elements, one of said elements comprising a protrusion and the other of said portions comprising means for defining a recess to receive said protrusion, said punch means for removably receiving a portion of the pouch between said elements with said waste receiving opening and said, mounting means aligned between said protrusion and said recess defining means and for removably inserting said protrusion through said waste receiving opening and removably punching said protrusion through said mounting means and the other of said walls affixed thereto so that said protrusion is removably received within said recess defining means and such that a vent is formed through said mounting means and said other of said walls affixed thereto, said mounting means for removable mounting of a filter over the vent when the portion of the pouch is removed from said punch means.

2. The device of claim 1 wherein said mounting means has a substantially annular configuration.

3. The combination of claim 1 wherein said mounting means is comprised of polyethylene and ethylene vinyl acetate.

4. The combination of claim 1 further comprising a filter and means for adhesively affixing said filter on said mounting means.

5. The combination of claim 1 wherein one of said elements comprises a substantially planar portion and a portion substantially perpendicular to said planar portion.

6. The combination of claim 5 further comprising a living hinge hingeably connecting said elements.

7. The combination of claim 6 wherein said living hinge is adjacent to said perpendicular portion.

8. The combination of claim 5 wherein said protrusion is substantially parallel to said perpendicular portion when said protrusion is received within said recess defining means.

9. The combination of claim 1 further comprising a living hinge hingeably connecting said elements.

* * * * *